United States Patent [19]

Zimmerman et al.

[11] Patent Number: 4,698,428

[45] Date of Patent: Oct. 6, 1987

[54] CATALYTIC METHOD FOR THE MANUFACTURE OF N,N′-DIMETHYLPIPERAZINE

[75] Inventors: Robert L. Zimmerman, Austin; Steven H. Vanderpool, New Braunfels, both of Tex.

[73] Assignee: Texaco Inc., White Plains, N.Y.

[21] Appl. No.: 871,954

[22] Filed: Jun. 9, 1986

[51] Int. Cl.$^4$ .................. C07D 241/04; C07C 85/06
[52] U.S. Cl. .................... 544/404; 564/479; 564/485; 564/509; 564/512
[58] Field of Search ............... 544/404; 564/479, 485, 564/509, 512

[56] References Cited

U.S. PATENT DOCUMENTS

| | | | |
|---|---|---|---|
| 3,037,025 | 5/1962 | Godfry | 544/404 |
| 3,159,633 | 12/1964 | Langdon et al. | 544/404 |
| 3,167,551 | 1/1965 | Neiport | 544/404 |
| 3,249,613 | 5/1966 | Burns et al. | 544/404 |
| 3,697,524 | 10/1972 | Tomalia et al. | 544/404 |
| 3,732,311 | 5/1973 | Baron | 544/404 |
| 4,036,881 | 7/1977 | Brennan et al. | 564/512 |
| 4,105,657 | 8/1978 | Dockner et al. | 544/404 |
| 4,316,840 | 2/1982 | Ford et al. | 564/512 |
| 4,588,842 | 5/1986 | Vanderpool | 564/512 |
| 4,647,664 | 3/1987 | Vanderpool | 564/479 |

FOREIGN PATENT DOCUMENTS 2316358  10/1974  Fed. Rep. of Germany ...... 544/404

OTHER PUBLICATIONS

Vanderpool, CA, 101-194142v.

Primary Examiner—Donald G. Daus
Assistant Examiner—Cecilia Shen
Attorney, Agent, or Firm—John H. Park; Kenneth R. Priem

[57] ABSTRACT

It has been surprisingly discovered in accordance with the present invention that N-methylethanolamine may be converted to N,N′-dimethylpiperazine when using a catalyst composed of titania to which from about 0.5 to about 7 wt. % of phosphorus has been thermally chemically bonded in the form of phosphate linkages.

3 Claims, No Drawings

CATALYTIC METHOD FOR THE MANUFACTURE OF N,N'-DIMETHYLPIPERAZINE

BACKGROUND OF THE INVENTION

1. Field of the Invention

This invention relates to a catalytic method for the preparation of N,N'-dimethylpiperazine. More particularly, this invention relates to a catalytic method for the manufacture of N,N'-dimethylpiperazine from N-methylethanolamine. Still more particularly, this invention is directed to the use of a titania catalyst to which a minor amount of phosphorus has been thermally chemically bonded at the surface thereof in the form of phosphate linkages. Even more particularly, the present invention is directed to a process for the manufacture of N,N'-dimethylpiperazine from N-methylethanolamine using a catalyst composed of titania to which a minor amount of phosphorus (0.5 to 7 wt. %) has been thermally chemically bonded to the surface in the form of phosphate linkages.

2. Prior Art

The catalysts used in the practice of the process of the present invention are disclosed in Vanderpool European patent application Ser. No. 83,307,520.3 published Aug. 28, 1984, wherein they are disclosed as useful in promoting the reaction of ethylenediamine with ethanolamine to provide essentially linear polyethylenepolyamine reaction products. Minor quantities of cyclic products are also formed.

It has heretofore been proposed to prepare N,N'-dimethylpiperazine by a variety of techniques. For example, Steele U. S. Patent No. 2,868,791 discloses a process for the preparation of N,N'-dimethylpiperazine by the pressured reaction of N-methylethanolamine with carbon dioxide. In the example, an aqueous solution of N-methylethanolamine was saturated with carbon dioxide and heated at 160°-170° C. for 20 hours at a pressure of 500-580 psia to provide a crude reaction mixture containing N,N'-dimethylpiperazine.

Godfrey U.S. Pat. No. 3,037,025 discloses a process for the preparation of N-alkyl substituted piperazines such as N,N'-dimethylpiperazine by reacting monoethanolamine with methylamine at an elevated temperature and pressure in the presence of a nickel, copper, chromia hydrogenation catalyst in the presence of hydrogen. There is a similar disclosure in Godfrey U.S. Pat. No. 3,037,025.

Schulze U.S. Pat. No. 4,066,649 discloses a process for the catalytic production of N,N'-(dimethyl) piperazines by reacting a primary 1-amino-2-alkanol such as monoethanolamine with methyl alcohol. The catalyst that is used is a phosphorus containing substance such as acidic metal phosphate, a compound of phosphorus or phosphoric acid, alkyl or aryl phosphate or phosphite esters.

A process for the production of N-alkylated cyclic alkyleneimines such as N-methyl piperazine from an alcohol such as methanol and a cyclic amine such as piperazine is disclosed in Dockner et al. U.S. Pat. No. 4,105,657. The catalyst is a high surface area $SiO_2$/$P_2O_5$ catalyst prepared, for example, by reacting 0.1 to 20% of phosphoric acid with a silic acid hydrogel.

SUMMARY OF INVENTION

It has been surprisingly discovered in accordance with the present invention that N-methylethanolamine may be converted to N,N'-dimethylpiperazine when using a catalyst composed of titania to which from about 0.5 to about 7 wt. % of phosphorus has been thermally chemically bonded in the form of phosphate linkages.

DETAILED DESCRIPTION OF THE EMBODIMENT

Feedstock

The feedstock to be used in accordance with the present invention is N-methylethanolamine.

Reaction Conditions

When the reaction is conducted in a batch reactor, the catalyst will preferably be employed in powdered form, whereas when the reaction is conducted on a continuous basis the catalyst is preferably employed in the form of pellets.

The reaction is suitably conducted at a temperature of about 260°-350° C. and, more preferably, at a temperature of about 280° to about 300° C.

The reaction is also preferably conducted at a superatmospheric pressure of about 500 to about 2000 psig. and more preferably at a pressure of about 1000 to about 1700 psig.

When the reaction is conducted on a batch basis, the reaction time may suitably vary from about 0.5 to about 5 hours. When the reaction is conducted on a continuous basis, the feedstock may suitably be passed over a bed of pelleted catalyst at a liquid hourly space velocity (lhsv) of about 0.5 to about 5 volumes of the aqueous solution of the amine feedstock per volume of catalyst per hour. More preferably, the lhsv will be from about 1 to about 3.

It is not necessary to use either ammonia or hydrogen as feed components in the practice of the process of the present invention.

Catalyst

The catalyst composition of the present invention is prepared by depositing a phosphorus compound on titania support as described in greater detail in copending Vanderpool application Ser. No. 06/564,153 filed Dec. 22, 1983, and entitled "Catalytic Preparation of Linear Polyethylenepolyamines" and in Vanderpool European patent application Ser. No. 83,387,520.3 published Aug. 24, 1984.

Any appropriate water soluble or liquid phosphorus compound can be used as a source of the phosphorus. For convenience, phosphoric acid will normally be used. However, other phosphorus compounds such as phosphoryl chloride ($POCl_3$), phosphorous acid, polyphosphoric acid, phosphorus halides, such as phosphorus bromide, alkyl phosphates and alkyl phosphites such as trimethyl phosphate, triethyl phosphate, trimethyl phosphite, triethyl phosphite, etc. may be utilized. Also, a diamminohydrogen phosphate such as diammonium hydrogen phosphate, $(NH_4)_2HPO_4$, dimethylamino hydrogen phosphate, $(CH_3)_2NH_2PO_4$, diethylaminohydrogen phosphate $(CH_3CH_2)_2NH_2PO_4$, etc. may be used.

A suitable procedure to be used is to heat a liquid containing the liquid or liquefiable phosphorus compound at a temperature of about 100° to about 150° C. and to then add powdered or pelleted titania in an amount about equal to the volume of the heated liquid. This treatment should be continued from about 0.5 to about 5 hours. At the end of that time, the resulting mixture is cooled, decanted to remove excess liquid followed by washing with an amount of water adequate to substantially completely remove unadsorbed liquid. Temperatures above 150° C. can be used, if desired, but there is no particular advantage in doing so.

It will be understood that the phosphorus that is present on a thus-treated catalyst is not present as elemental phosphorus, but rather as phosphorus that is chemically bound, probably as an oxide, to the titania. This is demonstrated by the fact that repeated washing will not remove all of the phosphorus. However, the exact nature of the bonding is not completely understood.

The amount of phosphorus that is bonded or otherwise adheres to the titania is a function of heating and other conditions used in the treating step and is also a function of the chemical identity of the phosphorus compound that is used as a source of phosphorus. Under the treating conditions exemplified above, at least about 0.5 wt % of phosphorus is caused to bond (i.e., permanently adhere) to the titania. There is an upper limit to the amount of phosphorus that bonds to the titania. This upper limit is, as indicated, a function of both the treating conditions and the chemical used as a source of the phosphorus. Normally, the maximum amount of phosphorus that can be caused to bond or otherwise permanently adhere to the titania is within the range of about 7 wt. %.

As a matter of convenience, the normal practice is to use only one chemical as a phosphorus source (e.g., phosphoric acid). However, mixtures of two or more such reagents may be used, if desired.

When the catalyst is to be used in pelleted form, pellets of titania can be impregnated with the phosphorus compound at a temperature of at least about 100° C., there is no absolute need to calcine the catalyst composition before use. However, the pellets can be calcined prior to use, if desired, as a precautionary measure and/or in order to still further improve the physical properties of the pellets. The pellets are suitably calcined at a temperature of about 200° C. to about 800° C. for a period of time within the range of 2 to 24 hours; more preferably at a temperature of about 300° C. to about 600° C. for about 4 to 16 hours.

Other procedures can be used in adding phosphorus to the titania. For example, the pellets can be treated with the phosphorus compound at ambient temperatures or at more modest elevated temperatures of less than about 100° C.

If the treatment is conducted at a temperature of about 100° C. or more, thermal activation will normally have been obtained and it will not be absolutely necessary to perform a calcining operation prior to use. If lower treating temperatures are used, calcining prior to use is normally a desired operation. The calcining operation can be conducted prior to or subsequent to the pelleting step.

In any event, in-situ calcining will occur when the phosphorus-titania composition is used to catalyze the conversion of N-methylethanolamine to N,N'-dimethylpiperazine at 260" to 350° C., as is hereinafter more fully set forth.

EXAMPLE

Equipment and Procedures

The evaluation was performed in a 100 cc reactor constructed of ⅜ inch stainless steel tubing connected to ⅛ inch feed and effluent lines with swagelok fittings. The reactor tube was situated inside of a 3×3 inch aluminum block which was heated electrically with four 1000 watt strip heaters. Temperature control was achieved with a Thermoelectric controller monitoring thermocouples attached to the skin of the reactor body. The feed was charged to the reactor system with a Beckman 110A L.C. pump. For safety, pressure relief was provided by a 3000 lb. rupture disk assembly although all runs were preformed at atmospheric pressure to minimize bimolecular reactions. The reactor effluent was collected in a glass jug and sampled after the system had lined-out at the proscribed temperature for at least 2.5 hours.

Analysis of the reactor effluent was achieved using an OV-17 column in a Hewlett-Packard 5710A gas chromatograph. Analysis was on a water-free and feed-free basis.

The tubular reactor was filled with about 100 cc of a titania-phosphorus catalyst containing about 2 wt. % of phosphorus thermally, chemically bonded to titania pellets prepared by the dipping of a preformed pellet into a 30% polyphosphorus acid solution, followed by decanting and calcination at 450° C.

Methylethanolamine was passed over the catalyst at the designated temperature and a reaction pressure of 1,500 psig. at the rate of 3.4 ml/min. The temperatures used and the results obtained are set forth below:

|  | Area Percent by G.C. | | |
| --- | --- | --- | --- |
| Reactor temperature | 250 C. | 270 C. | 290 C. |
| N,N'—Dimethylpiperazine | 1.8 | 58.1 | 62.0 |
| Unknown | — | 10.3 | 13.4 |
| Unknown | — | 2.5 | 2.5 |
| Methylethanolamine | 90.8 | 19.4 | — |
| Unknown | — | — | 3.9 |
| Unknown | 5.5 | — | — |

This example shows that N,N'-dimethylpiperazine can be prepared in good yield from N-methylethanolamine at temperatures above about 260° C.

The foregoing example is given by way of illustration only, and is not intended as a limitation on the scope of this invention, as defined by the appended claims.

What is claimed is:

1. A method for the manufacture of N,N'-dimethylpiperazine which comprises bringing a feedstock comprising N-methyldiethanolamine into contact with a cyclization catalyst at a temperature of about 260°–350° C. and a pressure within the range of about 500 to about 2000 psig. for a period of time sufficient to convert at least a portion of said N-methylethanolamine to N,N'-dimethylpiperazine, said catalyst composition consisting essentially of titania having from about 0.5 to about 7 wt. % of phosphorus thermally chemically bonded to the surface thereof in the form of phosphate bonds.

2. A method as in claim 1 wherein the temperature is within the range of about 260° to about 350° C. and the pressure is within the range of about 500 to about 2,000 psig.

3. A method as in claim 2 wherein the feedstock consists essentially of N-methylethanolamine.

* * * * *